United States Patent [19]
Adell

[11] Patent Number: 5,406,963
[45] Date of Patent: Apr. 18, 1995

[54] MOUTHGUARD

[76] Inventor: Loren S. Adell, 200 Adell Blvd., Sunnyvale, Tex. 75182

[21] Appl. No.: 24,854

[22] Filed: Feb. 26, 1993

Related U.S. Application Data

[63] Continuation of Ser. No. 780,545, Oct. 22, 1991, abandoned, which is a continuation of Ser. No. 616,329, Nov. 21, 1990, abandoned, which is a continuation of Ser. No. 329,407, Mar. 27, 1989, abandoned.

[51] Int. Cl.6 ............................................. A61C 5/14
[52] U.S. Cl. .................................. 128/861; 128/862
[58] Field of Search ............................ 128/859–862, 128/62 R; 433/34, 33, 36, 6; 2/2; 264/16, 240, 250, 255, 347

[56] References Cited

U.S. PATENT DOCUMENTS

| | | |
|---|---|---|
| 767,553 | 8/1904 | Edgelow . |
| 2,705,492 | 4/1955 | Chandler ............................. 128/862 |
| 2,706,478 | 4/1955 | Porter . |
| 2,833,278 | 5/1958 | Ross ..................................... 128/862 |
| 2,996,908 | 1/1961 | Cathcart et al. . |
| 3,060,935 | 10/1962 | Riddell . |
| 3,070,300 | 1/1963 | Berghash . |
| 3,124,129 | 3/1964 | Grossberg ........................... 128/862 |
| 3,211,143 | 10/1965 | Grossberg ........................... 128/862 |
| 3,223,085 | 12/1965 | Gores et al. . |
| 3,250,272 | 5/1966 | Greenberg ........................... 128/862 |
| 3,303,844 | 2/1967 | Johnson et al. . |
| 3,312,218 | 4/1967 | Jacobs . |
| 3,333,582 | 8/1967 | Cathcart . |
| 3,355,526 | 11/1967 | Molnar . |
| 3,411,501 | 11/1968 | Greenberg ........................... 128/862 |
| 3,416,527 | 12/1968 | Hoef . |
| 3,457,916 | 7/1969 | Wolicki ............................... 128/862 |
| 3,505,995 | 4/1970 | Greenberg . |
| 3,527,219 | 9/1970 | Greenberg . |
| 3,532,091 | 10/1970 | Lerman . |
| 3,844,286 | 10/1974 | Cowen . |
| 3,924,638 | 12/1975 | Mann . |
| 3,943,924 | 3/1976 | Kallestad et al. . |
| 4,063,552 | 12/1977 | Going et al. . |
| 4,350,154 | 9/1982 | Feldbau . |
| 4,448,735 | 5/1984 | Huge .................................... 264/16 |
| 4,569,342 | 2/1986 | von Nostitz . |
| 4,848,365 | 7/1989 | Guarlotti ............................. 128/862 |
| 4,920,984 | 5/1990 | Furumichi et al. . |
| 4,955,393 | 9/1990 | Adell ................................... 128/862 |
| 5,031,638 | 7/1991 | Castaldi . |
| 5,082,007 | 1/1992 | Adell . |
| 5,103,838 | 4/1992 | Yousif . |

OTHER PUBLICATIONS

ELVAX–Resins for Molding, Compounding, and Extrusion–A Grade Selection Guide (5 pages) by DuPont.
ELVAX Price List Effective Apr. 1, 1990 by DuPont (2 pages).
ELVAX–40–W High Vinyl Acetate Resin–Technical Information (2 pages) by DuPont.

Primary Examiner—Michael A. Brown
Attorney, Agent, or Firm—George L. Boller

[57] ABSTRACT

A method of making a mouthguard by fabricating a relatively more rigid main body of a material, such as ethylene/vinyl acetate copolymer for example, and directly molding onto the troughs of the main body a liner which is of a relatively less rigid material, such as ethylene/vinyl acetate copolymer for example, that bonds directly to the material of the main body to form a mouthguard in which the trough liner is tooth-impressionable after having been so bonded. The mouthguard has a tri-laminar occlusal wall composed of the lower durometer liner sandwiching the higher durometer main body material, and the mouthguard exhibits surprising impact-absorbing characteristics that are helpful in protecting certain cranio-facial bone structure in response to certain impacts.

6 Claims, 2 Drawing Sheets

MOUTHGUARD

REFERENCE TO A RELATED APPLICATION

This application is a continuation-in-part of my application Ser. No. 07/780,545, filed Oct. 22, 1991, now abandoned, which is a continuation of my now-abandoned application Ser. No. 07/616,329, filed Nov. 21, 1990, which is a continuation of my now-abandoned application Ser. No. 07/329,407, filed Mar. 27, 1989.

FIELD OF THE INVENTION

This invention relates to a method of making a mouthguard.

BACKGROUND AND SUMMARY OF THE INVENTION

My issued U.S. Pat. No. 4,955,393, discloses certain improvements in mouthguards. The invention which is the subject of this application relates to a method for making the mouthguard that is described in U.S. Pat. No. 4,955,393, and to other mouthguards of the type in which a relatively more rigid main body having at least one trough for a dental arch contains a relatively less rigid liner material in the trough.

In addition to the features that have already been disclosed in the mouthguard that is the subject of U.S. Pat. No. 4,955,393, I have discovered that unexpected beneficial results can be obtained in a mouthguard by fabricating the mouthguard in a particular way. Specifically, I have found that by making the trough liner of the same, but lower durometer material as the main body material, it is possible to join the liner and main body together by bonding without the use of separate adhesive or other means of mechanical joining, and that the resulting mouthguard will exhibit a surprising improvement in impact absorption when in use. This attribute has been demonstrated by comparative testing with mouthguards of other, different constructions.

I have further discovered that principles of my invention can be practiced with certain liner materials and certain main body materials other than materials which are identical except for durometer. This endows the inventive principles with a generic character that is not limited to the particular materials involved. According to this generic character, the liner and the main body materials are ones which will directly bond together without the use of separate adhesive or other means of mechanical attachment when the liner material is molded directly onto the main body material, and the liner material is one which is tooth-impressionable after it has been directly molded onto the main body.

While the prior art has recognized the disadvantage of using separate adhesive or other means of mechanically attaching a mouthguard liner to a mouthguard body (see Wolicki U.S. Pat. No. 3,457,916), the advantage of directly joining the liner to the main body by allowing liner material to cure onto the main body (see Wolicki U.S. Pat. No. 3,457,916 and Ross U.S. Pat. No. 2,833,278), and the desirability of having a main body which is tooth-impressionable after the molding thereof (see Greenberg U.S. Pat.No. 3,505,995), no one has heretofore conceived of a method for making a mouthguard in which a liner material is molded directly onto a relatively more rigid main body for bonding thereto without the use of separate adhesive or other means of mechanical attachment and in which the liner thus formed is both relatively less rigid than the main body and also tooth-impressionable after it has been so bonded to the main body.

The various aspects of my invention will be described in greater detail in the ensuing description which is accompanied by drawings and presents a presently preferred embodiment of the invention in accordance with the best mode contemplated at this time in carrying out the invention.

DESCRIPTION OF THE PREFERRED EMBODIMENT

Figure 1:
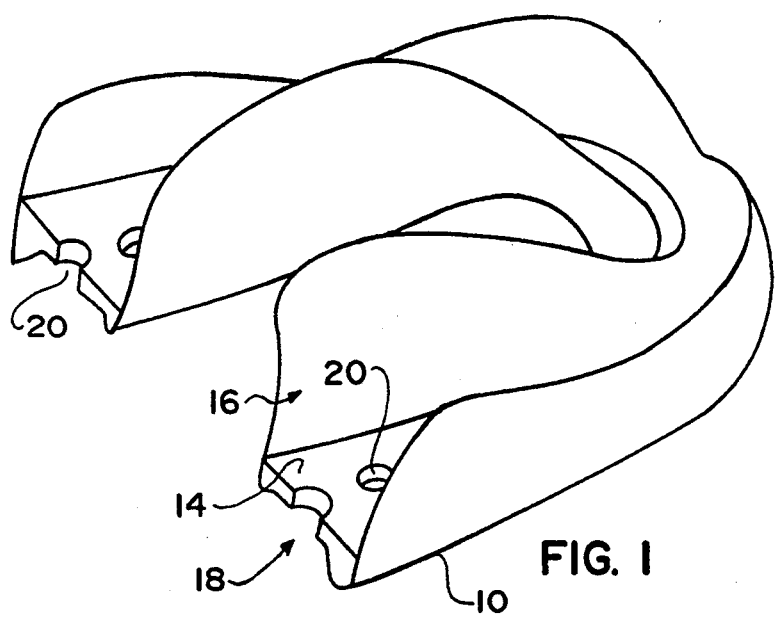
FIG. 1 is a perspective view from the rear right side showing the main body of a mouthguard.
Figure 2:
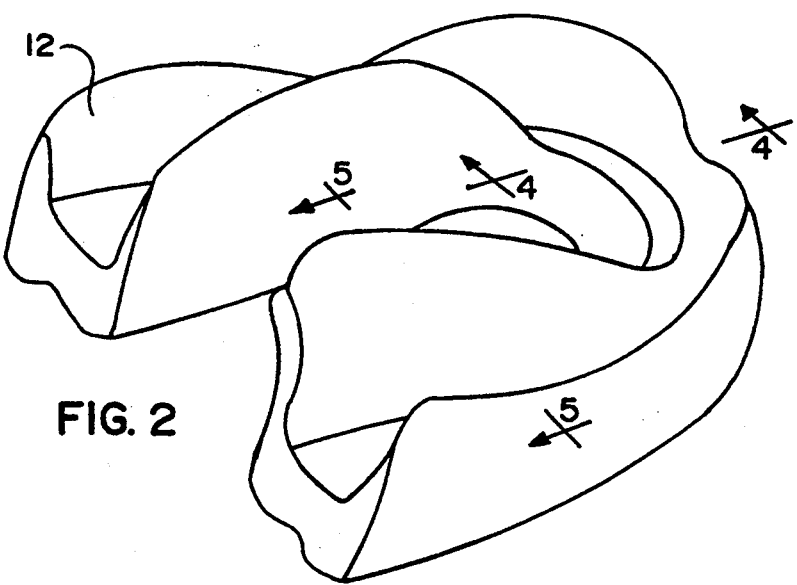
FIG. 2 is a view similar to FIG. 1 showing the completed mouthguard after liner material has been applied to the main body.
Figure 3:
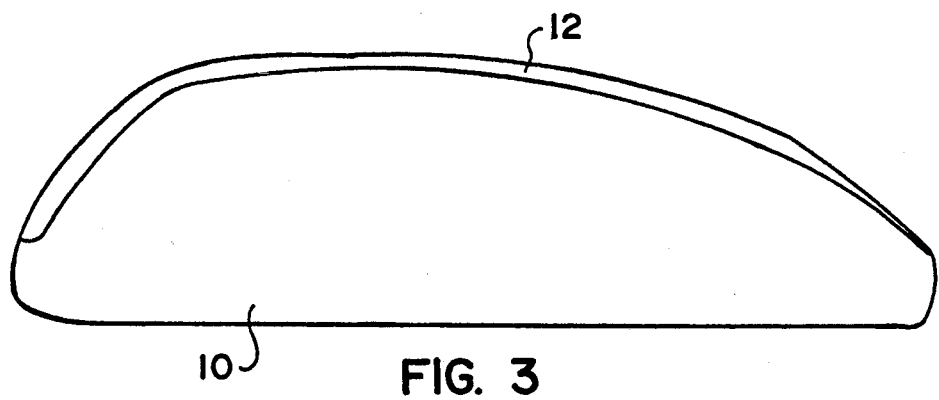
FIG. 3 is a side lingual view.

In the drawings, FIG. 1 shows the main body 10 which comprises a general U-shape for fitting into the mouth. It is onto this main body 10 that a liner 12 is molded to complete the mouthguard as shown in FIG. 2.

Figure 4:
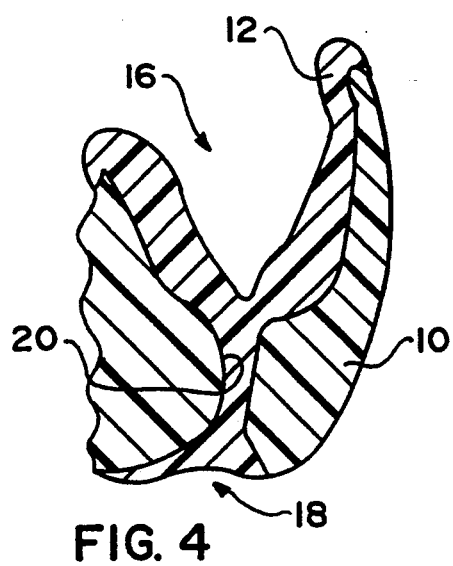
FIG. 4 is a cross-sectional view taken approximately along line 4—4 in FIG. 2.
Figure 5:
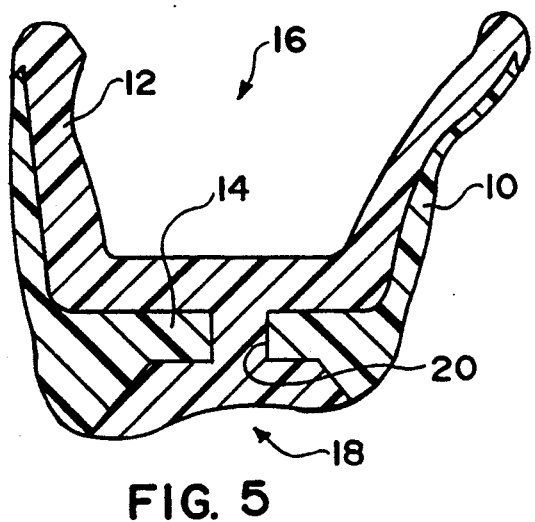
FIG. 5 is a cross-sectional view taken approximately along line 5—5 in FIG. 2.

Main body 10 comprises an occlusal wall 14 and troughs 16 and 18 on opposite sides. The troughs are for the upper arch and the lower arch respectively. Trough 16 is fairly deep while trough 18 is quite shallow. There are a series of spaced apart through-holes 20 extending through occlusal wall 14, and in FIG. 1 the rear ends of the mouthguard main body are cut away for illustration. In FIGS. 2, 4, and 5, it can be seen that liner 12 has been molded onto main body 10.

Liner 12 lines the full interior of both troughs 16 and 18. The liner material also passes through through-holes 20 so that the material that lines trough 16 joins with the material lining trough 18. In other words, the material lining one trough is integrally joined with the material lining the other trough.

The process for making the mouthguard comprises, first, fabricating the main body. In accordance with certain principles of the invention, the main body is fabricated from a particular molding material of a particular durometer. One preferred molding material is ethylene/vinyl acetate copolymer, such as that sold commercially under the brand name Elvax. The main body can be molded by any suitable process, but it is desired that the finished main body have a comparatively higher durometer than the finished liner. For example, a main body with a durometer of 90 is quite suitable, although it is to be understood that this is just an example.

Liner 12 is molded directly onto main body 10 by an injection molding process. By making liner 12 of the same material as the main body (i.e. ethylene/vinyl acetate copolymer), there is a chemical compatibility between the two which allows an intimate bonding of the liner to the main body to occur without the use of separate adhesive or other mechanical means of attachment; yet according to further principles of the invention, the durometer of liner 12 is made relatively lower than that of main body 10, whereby liner 12 is relatively softer. For example, a durometer of 40 is quite satisfactory, although it may range from 30 to 50 and still produce acceptable results. The particular durometers for the main body and for the liner are attained by conventional formulation procedures.

According to further principles of the invention, liner 12 is tooth-impressionable after having been bonded to the main body. When the mouthguard is put to use, this enables the liner to conform to the teeth of the arch, and the teeth to be comfortably, yet securely received in the liner. It is desirable to mold the liner onto the main body while the main body is still warm since this is believed to create a more intimate bonding; however, this may not be essential in all instances since the materials are identical.

The result of the just-described process is that a tri-laminar construction is created for the occlusal wall of the finished mouthguard. This tri-laminar construction comprises the same material (ethylene/vinyl acetate copolymer) forming the occlusal wall, wherein two layers of lower durometer sandwich a layer of higher durometer. It is this construction that contributes to the surprising impact absorbing properties of the mouthguard that have been demonstrated by laboratory testing. It should be understood that the main body can contain an insert and the construction of the mouthguard is still considered tri-laminar.

My further work has identified additional combinations of liner/main body materials that can be used in the practice of my method. Ethylene/vinyl acetate copolymer will bond directly to polyvinyl chloride, to polyurethane, to thermoplastic rubber, and to low density polyethylene. Vinylidene chloride will bond directly to ethylene/vinyl acetate copolymer. Polyvinyl acetate will bond directly to a higher durometer ethylene/vinyl acetate copolymer. Thus a main body can be made using polyvinyl chloride, polyurethane, thermoplastic rubber, low density polyethylene, or ethylene/vinyl acetate copolymer, and the mouthguard may be completed by directly molding an appropriate liner material to the main body to form the liner. A mouthguard can also be fabricated by making a main body of a higher durometer polyvinyl chloride and directly molding a lower durometer polyvinyl chloride directly onto the main body. It is best if the molding of the liner to the main body is conducted sufficiently soon after the main body has been fabricated in order to avoid the migration of plasticizer to the main body's surface because the presence of an excessive amount of plasticizer at the surface may impair the integrity of the bonding of the liner to the main body in the case of certain liner materials, such as ethylene/vinyl acetate copolymer.

The invention is well suited for the commercial mass-production of mouthguards which are marketed through commercial channels, such as sporting goods stores and sports departments of department stores. While a presently preferred embodiment has been disclosed, it should be appreciated that principles of the invention may be practiced in other ways that are equivalent to the following claims.

What is claimed is:

1. A mouthguard comprising a main body having an ethylene vinyl acetate (EVA) occlusal wall having upper and lower surfaces, a tooth-impressionable upper EVA liner lining said upper surface and into which teeth of an upper dental arch are to be impressed, a tooth-impressionable lower EVA liner lining said lower surface and into which teeth of a lower dental arch are to be impressed, said EVA occlusal wall having a durometer that is higher than the durometer of each of said liners, characterized in that said liners have durometers that are no higher than 40 durometer and in that said liners are directly injection-molded to said occlusal wall without the use of separate adhesive.

2. A mouthguard as set forth in claim 1 characterized further in that said occlusal wall comprises a series of through-holes and said liners are integrally joined with each other through said series of through-holes.

3. A mouthguard as set forth in claim 1 characterized further in that both said liners have the same durometer.

4. A mouthguard as set forth in claim 1 characterized further in that said occlusal wall has a durometer of at least 90.

5. A mouthguard as set forth in claim 1 characterized further in that said main body comprises EVA buccal and lingual wall means and at least one of said liners also lines said buccal and lingual wall means.

6. A tooth-impression device comprising a main body having an ethylene vinyl acetate (EVA) occlusal wall, tooth-impressionable EVA liner lining a surface of said occlusal wall and into which teeth of a dental arch are to be impressed, said EVA occlusal wall having a durometer that is higher than the durometer of said liner, characterized in that said liner has a durometer that is no higher than 40 durometer and in that said liner is directly injection-molded to said occlusal wall without the use of separate adhesive.

* * * * *